(12) United States Patent
Chen et al.

(10) Patent No.: US 12,048,580 B2
(45) Date of Patent: Jul. 30, 2024

(54) METHOD, SYSTEM AND PROGRAM PRODUCT FOR EVALUATING INTESTINAL FUNCTION USING BOWEL SOUNDS

(71) Applicant: CHIMEI MEDICAL CENTER, Tainan (TW)

(72) Inventors: Jen-Yin Chen, Tainan (TW); Bor-Shyh Lin, Tainan (TW)

(73) Assignee: Chimei Medical Center, Tainan (TW)

( * ) Notice: Subject to any disclaimer, the term of this patent is extended or adjusted under 35 U.S.C. 154(b) by 645 days.

(21) Appl. No.: 17/227,100

(22) Filed: Apr. 9, 2021

(65) Prior Publication Data
US 2022/0323041 A1  Oct. 13, 2022

(51) Int. Cl.
*A61B 7/00* (2006.01)
*A61B 7/02* (2006.01)
(Continued)

(52) U.S. Cl.
CPC ................ *A61B 7/008* (2013.01); *A61B 7/04* (2013.01); *G10K 11/17854* (2018.01);
(Continued)

(58) Field of Classification Search
CPC .. A61B 7/008; A61B 7/04; A61B 7/02; G10K 11/17854; G10K 11/17873;
(Continued)

(56) References Cited

U.S. PATENT DOCUMENTS

| | | | | |
|---|---|---|---|---|
| 4,387,722 A | * | 6/1983 | Kearns | A61B 5/0809 600/529 |
| 2016/0199020 A1 | * | 7/2016 | Sheu | A61B 7/008 600/586 |

(Continued)

FOREIGN PATENT DOCUMENTS

| | | |
|---|---|---|
| CN | 104305961 A | 1/2015 |
| CN | 106691498 A | 5/2017 |

(Continued)

OTHER PUBLICATIONS

Sheu et al., "Higher-Order-Statistics-Based Fractal Dimension for Noisy Bowel Sound Detection", IEEE, 22(7), 789-793, 2015 (Year: 2015).*

(Continued)

*Primary Examiner* — Matthew Kremer
*Assistant Examiner* — Jonathan Drew Moroneso
(74) *Attorney, Agent, or Firm* — Rosenberg, Klein & Lee

(57) ABSTRACT

A method, a system and a program product for evaluating an intestinal function using bowel sounds are disclosed. The method comprises the following steps: A. continuously monitoring an abdominal cavity of an examinee within a specific time by using an audio collection apparatus, collecting a bowel sound signal of an intestinal tract inside the abdominal cavity, and converting the bowel sound signal into a digital signal; B. using higher-order statistics (HOS), by a processing unit, to remove noise from the digital signal; C. using a fractal dimension algorithm, by the processing unit, to capture a high-complexity feature from the digital signal, and defining the high-complexity feature as an intestinal motility signal, and D. evaluating the intestinal function of the examinee, by the processing unit, according to the intestinal motility signal.

9 Claims, 9 Drawing Sheets

(51) Int. Cl.
*A61B 7/04* (2006.01)
*G10K 11/178* (2006.01)
*G10L 21/0232* (2013.01)
*G10L 25/66* (2013.01)
*H04R 1/46* (2006.01)
*G10L 21/0216* (2013.01)

(52) U.S. Cl.
CPC .... *G10K 11/17873* (2018.01); *G10L 21/0232* (2013.01); *G10L 25/66* (2013.01); *H04R 1/46* (2013.01); *A61B 7/02* (2013.01); *G10K 11/17821* (2018.01); *G10K 2210/116* (2013.01); *G10K 2210/3011* (2013.01); *G10K 2210/3027* (2013.01); *G10K 2210/3028* (2013.01); *G10L 2021/02163* (2013.01)

(58) Field of Classification Search
CPC ....... G10K 11/17821; G10K 2210/116; G10K 2210/3011; G10K 2210/3027; G10K 2210/3028; G10K 11/17823; G10L 21/0232; G10L 25/66; G10L 2021/02163; H04R 1/46
See application file for complete search history.

(56) References Cited

U.S. PATENT DOCUMENTS

2019/0216384 A1* 7/2019 Duval .................... A61B 7/008
2021/0259560 A1* 8/2021 Venkatraman .......... A61B 5/024
2022/0233119 A1* 7/2022 Shelton, IV ..... A61B 17/07207

FOREIGN PATENT DOCUMENTS

TW    201618717 A    6/2016
TW    201822711 A    7/2018

OTHER PUBLICATIONS

Flockett, "How to use a voltage reference for an accurate data conversion", Electronic Specifier, published on Aug. 29, 2019, accessed on Nov. 12, 2023, accessed at www.electronicspecifier.com/products/power/how-to-use-a-voltage-reference-for-an-accurate-data-conversion (Year: 2019).*

* cited by examiner

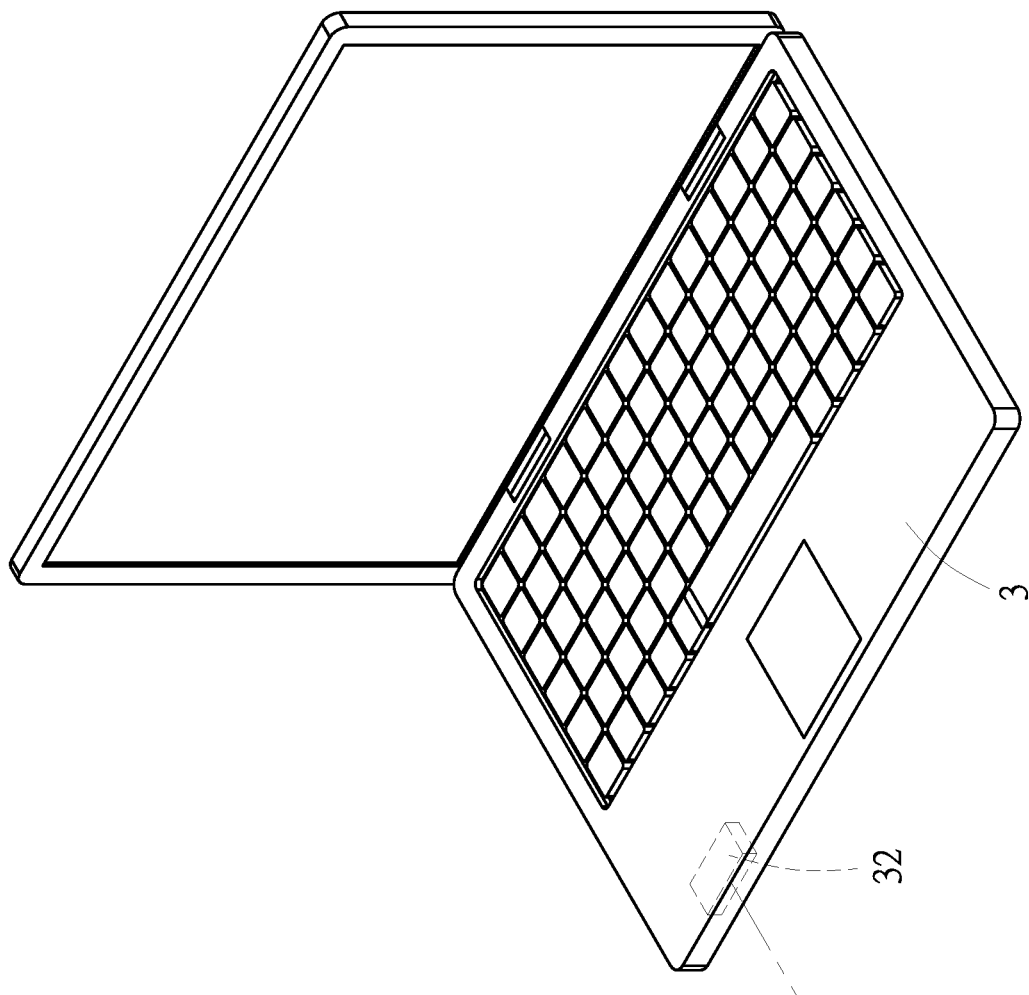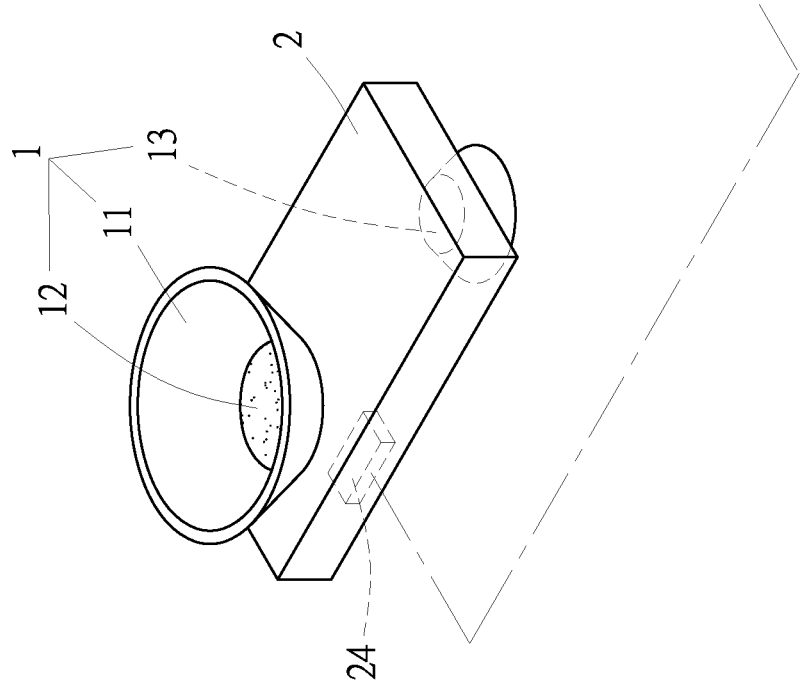
FIG. 1 collecting a bowel sound signal of an examinee by using an audio collection apparatus, and removing environmental noise by using an active noise cancellation (ANC) module in the process;

↓ asignal processing module converting the bowel sound signal into a digital signal, and the digital signal being sent to a back-end server;

↓ the server removing Gaussian noise from the digital signal by using higher-order statistics (HOS) and keeping non-Gaussian bowel sound information;

↓ the server using a fractal dimension algorithmto capture fractal dimension values from the digital signal; wherein the server captures a plurality of local maxima of the fractal dimension values, and the sum of an average value and a standard deviation of the local maxima serves as a threshold;

↓ when any one of the local maxima of the fractal dimension values exceeds the threshold, the server defining it as an intestinal motility signal;

↓ the server capturing at least one feature value of the intestinal motility signal and using artificial intelligence of a linear or non-linear algorithm for training to actively evaluate the intestinal function of the examinee

FIG. 3

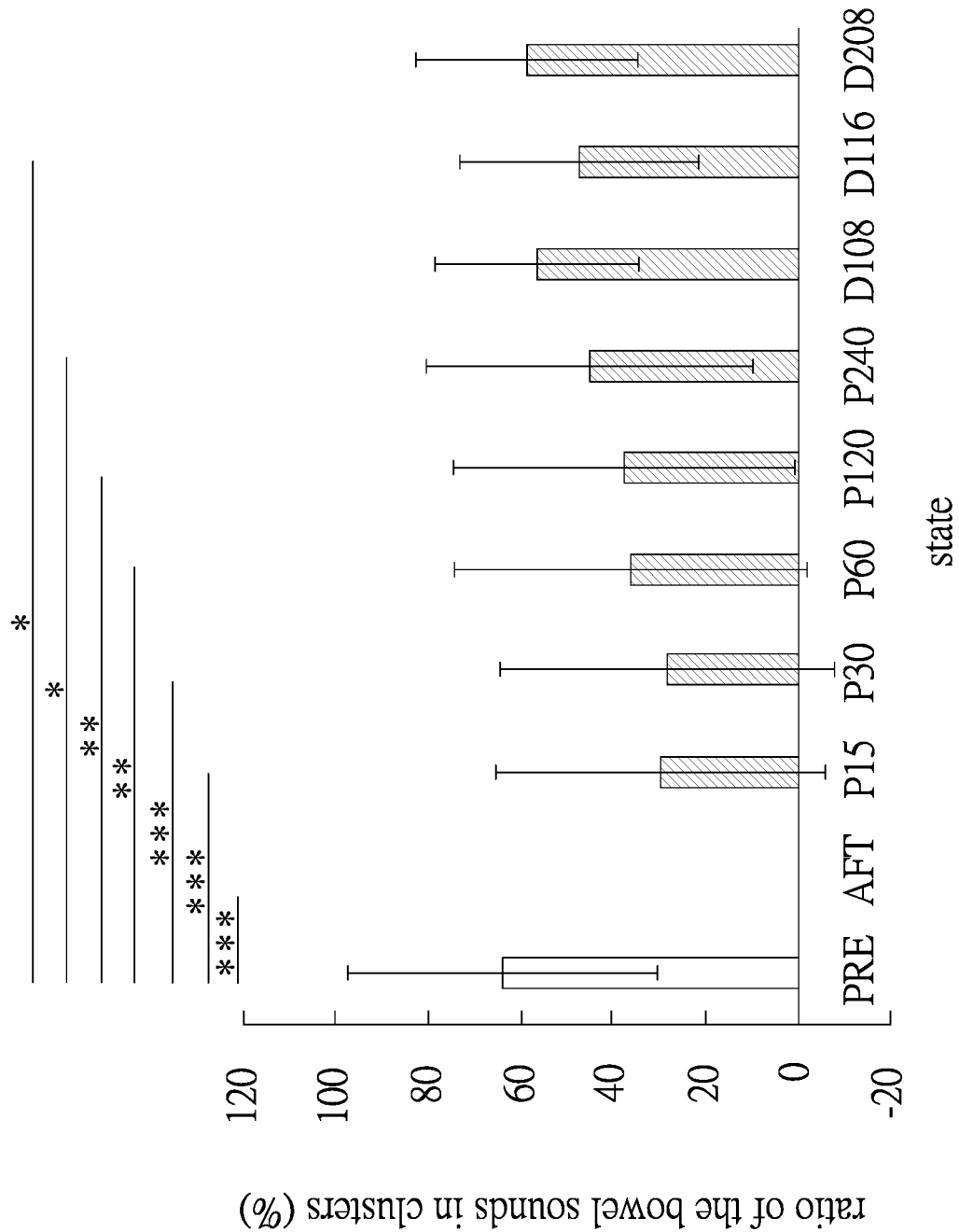
F I G. 6

METHOD, SYSTEM AND PROGRAM PRODUCT FOR EVALUATING INTESTINAL FUNCTION USING BOWEL SOUNDS

FIELD OF THE INVENTION

The present invention relates to a method, a system and a program product for evaluating an intestinal function using bowel sounds, and more particularly to a method that collects bowel sound signals of an examinee and removes noise by using higher-order statistics and then captures an intestinal motility signal by using a fractal dimension algorithm and further uses a linear or non-linear system to automatically predict and evaluate the intestinal function.

BACKGROUND OF THE INVENTION

In general, a physician judges the intestinal function of a patient through the state of intestinal motility. For example, before surgery, a patient usually receives general anesthesia with volatile or intravenous anesthetics. Because of the temporary suppression of intestinal motility by volatile and intravenous anesthetics, approximately one-third of patients may experience postoperative nausea and vomiting. However, after a medium or large operation, the patient should start eating again to get enough nutrition as soon as possible. Inappropriate fasting may result in insufficient protein intake, delayed healing of surgical wounds, decreased immune system, prolonged hospital stay and increased medical expenses. Therefore, physicians often evaluate the recovery state of the intestinal function through the patient's intestinal motility.

There are several traditional subjective methods for evaluating postoperative bowel recovery, such as eating after emitting gas from the anus or intestinal motility after surgery, eating early after surgery and auscultation. After emitting gas from the anus or intestinal motility after surgery, the patient gradually starts to have his/her normal diet by drinking water. The way to eat early after surgery is to start drinking fluids within 24 hours after surgery. If the patient is well (no symptoms of nausea and vomiting), the patient starts to have a normal diet of solid foods. However, eating before the recovery of the intestinal function is more likely to cause postoperative nausea, vomiting or abdominal distension for surgical patients. The way to eat early after surgery as a method of evaluating the intestinal function increases the risk of postoperative nausea, vomiting or abdominal distension. The method of auscultation is to auscultate the bowel sounds of the patient after surgery by a professional doctor to evaluate the recovery state of the intestinal function of the patient after surgery. But, this method is susceptible to environmental noise.

Taiwan Patent No. I579837 discloses a "Wireless Digital Bowel Sound Monitoring System", including a bowel sound sampling unit, a noise sampling unit, an audio filter processor, an analog-to-digital signal conversion unit, a wireless signal transmitter, and a server. After the bowel sounds are obtained by the bowel sound sampling unit and processed to remove noise, a frequency value of the bowel sounds can be obtained. When the frequency value of the bowel sounds exceeds a preset range, a warning device is controlled to send a warning signal.

In Taiwan Patent No. I535418, titled "Bowl Sound Analysis Method and System" and filed by the inventor, a bowel sound analysis method comprises the following steps: continuously monitoring an abdominal cavity of an examinee by using an audio collection apparatus, and collecting a bowel sound signal of an intestinal tract inside the abdominal cavity; converting the bowel sound signal into a digital signal; using higher-order statistics to remove noise from the digital signal; using a fractal dimension algorithm to capture a high-complexity feature from the digital signal, and defining the high-complexity feature as an intestinal motility signal. Therefore, according to the intestinal motility signal, a time point when intestinal motility occurs in the intestinal tract inside the abdominal cavity of the examinee can be learned, and bowel sound features such as the amplitude, frequency, and period of the intestinal motility signal may further be analyzed to determine a health condition of the intestinal tract.

SUMMARY OF THE INVENTION

In order to improve the accuracy of automatic detection of bowel sounds, the primary object of the present invention is to provide a method for evaluating an intestinal function using bowel sounds, comprising the following steps: A. continuously monitoring an abdominal cavity of an examinee within a specific time by using an audio collection apparatus, collecting a bowel sound signal of an intestinal tract inside the abdominal cavity, and converting the bowel sound signal into a digital signal; B. using higher-order statistics (HOS), by a processing unit, to remove noise from the digital signal; C. using a fractal dimension algorithm, by the processing unit, to capture a high-complexity feature from the digital signal, and defining the high-complexity feature as an intestinal motility signal, wherein the processing unit captures a plurality of local maxima of fractal dimension values, the sum of an average value and a standard deviation of the local maxima serves as a threshold, when any one of the local maxima of the fractal dimension values exceeds the threshold, it is regarded as the intestinal motility signal; and D. evaluating the intestinal function of the examinee, by the processing unit, according to the intestinal motility signal.

Preferably, in Step C, the processing unit captures the local maxima between 40% and 60% of the fractal dimension values.

Preferably, in Step D, the processing unit captures at least one feature value of the intestinal motility signal for evaluating the intestinal function of the examinee. The feature value includes an event frequency, sound index, ratio of the bowel sounds in clusters, duration, maximum peak value, and center frequency.

Preferably, in Step D, the processing unit uses a linear or non-linear algorithm to evaluate the intestinal function of the examinee. Preferably, the processing unit uses an artificial neural network to evaluate the intestinal function of the examinee. An evaluation value of the artificial neural network is set between 0 and 1. The number of hidden neurons and a judgment threshold are set to 64 and 0.4, respectively. Preferably, the processing unit captures the event frequency, sound index, ratio of the bowel sounds in clusters in the feature value to evaluate a postoperative recovery state of the intestinal function. Alternatively, the processing unit captures a duration, maximum peak value and center frequency in the feature value to evaluate acute enteritis, intestinal obstruction and irritable bowel syndrome in children.

The present invention further provides a system for evaluating an intestinal function using bowel sounds, comprising an audio collection apparatus, a signal processing module, and a server. The audio collection apparatus includes a stethoscope and a microphone. The stethoscope continuously collects a bowel sound signal within a specific time. The microphone converts the bowel sound signal into an electric signal. The signal processing module is connected to the audio collection apparatus. The signal processing module includes a preamplification circuit, a voltage reference circuit, a microprocessor, and a first transmission unit. The microprocessor has an analog-to-digital converter. The preamplification circuit amplifies and filters the electric signal. The microprocessor converts the electric signal into a digital signal and sends the digital signal through the first transmission unit. The server has a processing unit and a second transmission unit. The processing unit receives the digital signal from the first transmission unit through the second transmission unit, uses higher-order statistics (HOS) to remove noise from the digital signal, uses a fractal dimension algorithm to capture a high-complexity feature from the digital signal, and defines the high-complexity feature as an intestinal motility signal. The processing unit captures a plurality of local maxima of fractal dimension values. The sum of an average value and a standard deviation of the local maxima serves as a threshold. When any one of the local maxima of the fractal dimension values exceeds the threshold, it is regarded as the intestinal motility signal. The processing unit further evaluates the intestinal function of an examinee according to the intestinal motility signal.

Preferably, the audio collection apparatus further includes an active noise cancellation module.

The present invention further provides a program product, installed to a server, for performing the foregoing method.

According to the above technical features, the following effects can be achieved:

1. The invention uses auscultation technology to automatically monitor bowel sound signals and automatically evaluate intestinal function. In the bowel sound analysis algorithm, the fractal dimension technology based on high-order statistics can remove the environmental noise and keep the bowel sounds, so as to effectively detect and capture the feature values of the intestinal motility signal.

2. According to experiments, in the feature values captured from the intestinal motility signal, including the event frequency, sound index, ratio of the bowel sounds in clusters, are significantly different between the preoperative state and the postoperative recovery state, and can be used to evaluate the recovery state of the intestinal function after surgery. The feature values, such as the duration, maximum peak value and center frequency can be used to evaluate the symptoms of acute enteritis, intestinal obstruction and irritable bowel syndrome in children.

3. In the calculation of the fractal dimension of the bowel sound analysis algorithm, the present invention captures the local maxima between 40% and 60% of the fractal dimension values for prediction. This can reduce the influence of false bowel sound events caused by noise.

4. The present invention can effectively evaluate the intestinal function of the examinee through the feature values with significant changes by artificial intelligence training.

5. When the artificial intelligence prediction of the present invention adopts an artificial neural network, the evaluation value of the artificial neural network (RBFNN) is set between 0 and 1. The number of hidden neurons and a judgment threshold are set to 64 and 0.4, respectively, to obtain the best performance. (F measure=83.36%, sensitivity=96.25%, PPV=73.51%, accuracy=79.36%).

BRIEF DESCRIPTION OF THE DRAWINGS

The present disclosure will become more fully understood from the detailed description given herein below for illustration only, and thus are not limitative of the present disclosure, and wherein:

FIG. 1 is an architecture view of a system according to an embodiment of the present invention;

FIG. 3 is a flow chart of a method according to an embodiment of the present invention;

FIG. 6 is a bar graph showing the result of the ratio of the bowel sounds in clusters corresponding to the bowel recovery at different times after the limb surgery according to an embodiment of the present invention;

DETAILED DESCRIPTION OF THE PREFERRED EMBODIMENTS

In combination with the foregoing technical features, the major efficacy of a method, system, and program product for evaluating an intestinal function using bowel sounds of the present invention is clearly presented in the following embodiments.

Figure 2:
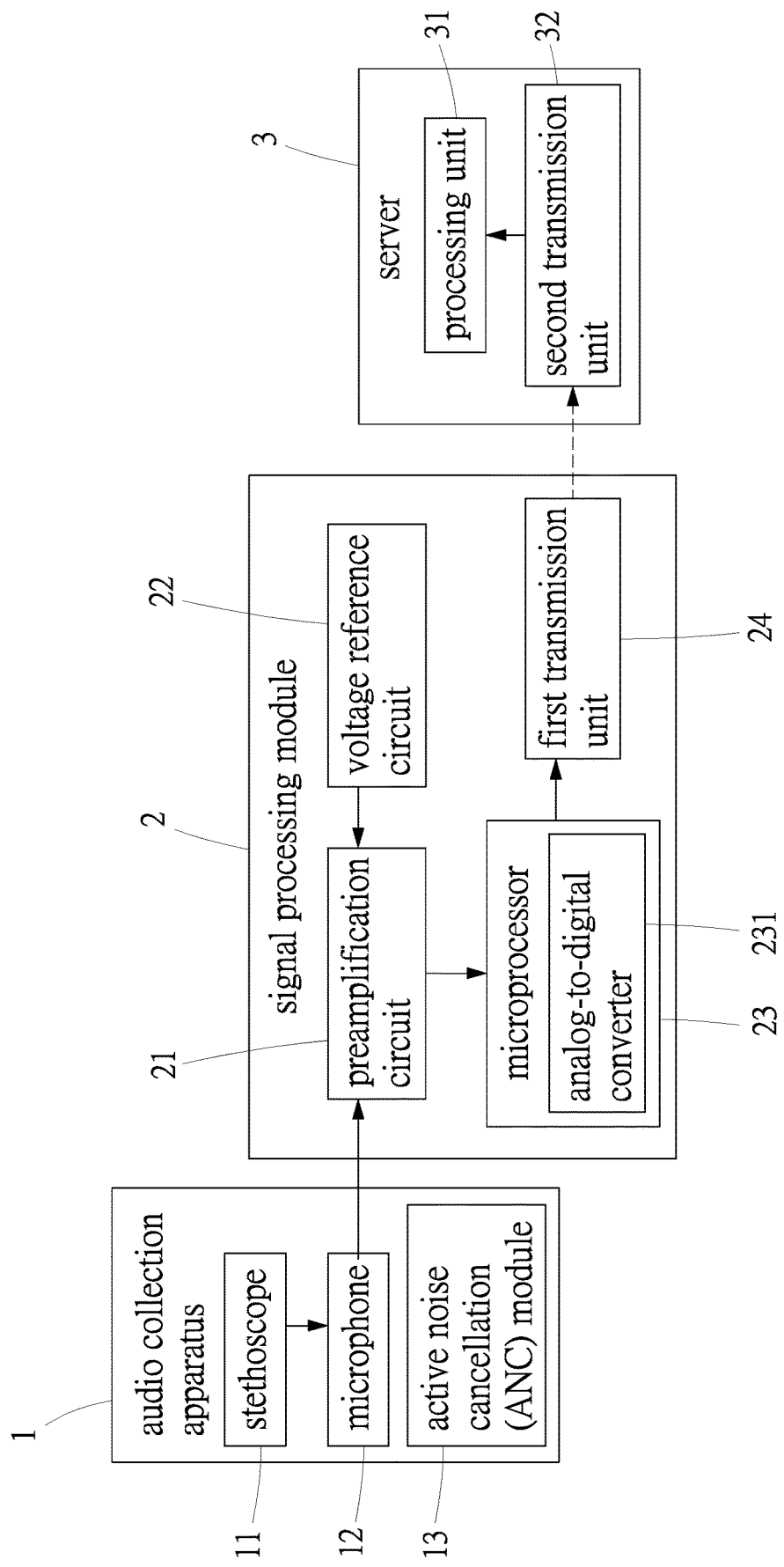
FIG. 2 is a functional block diagram of a system according to an embodiment of the present invention.
Figure 4:
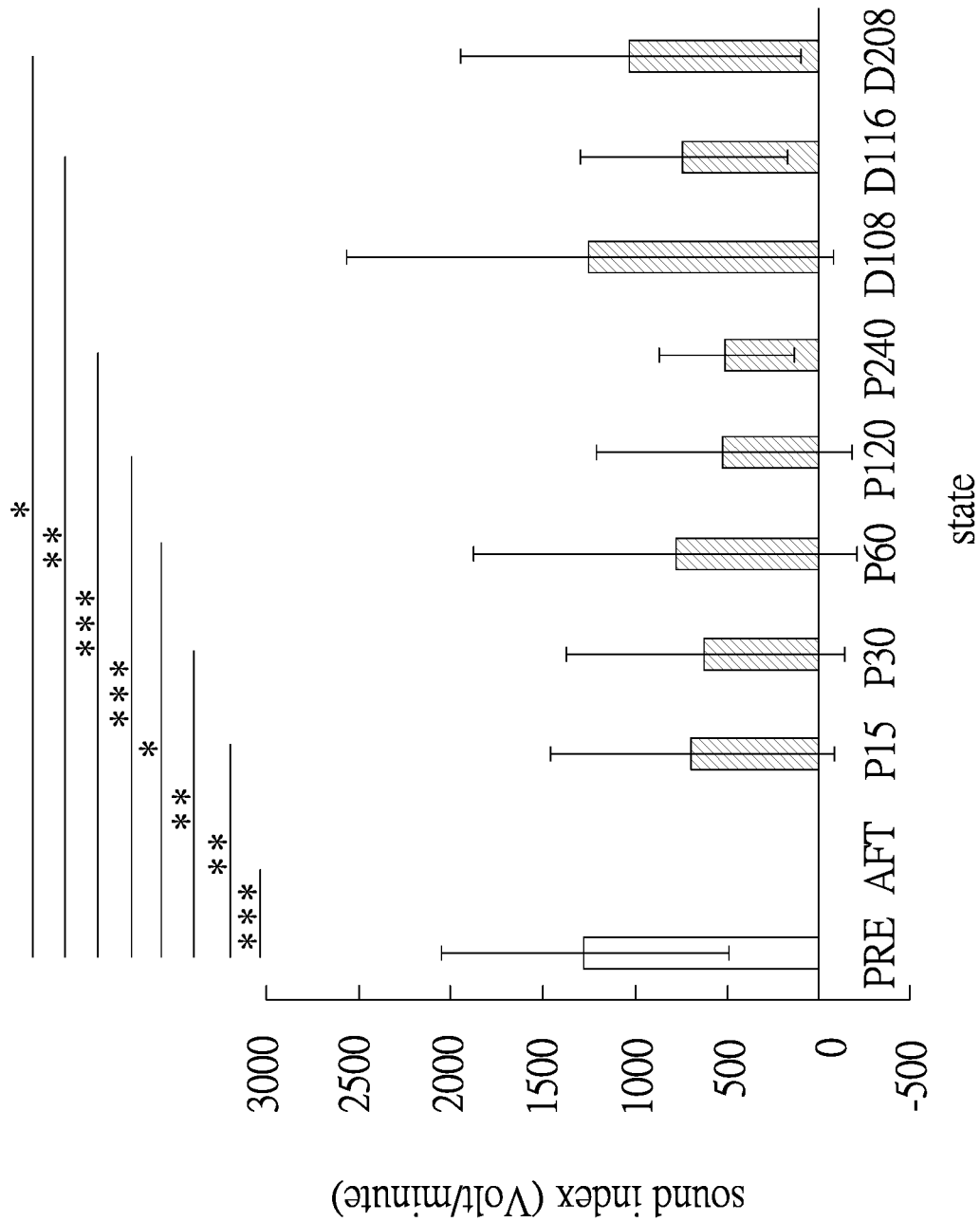
FIG. 4 is a bar graph showing the result of the sound index corresponding to the bowel recovery at different times after the limb surgery according to an embodiment of the present invention.
Figure 5:
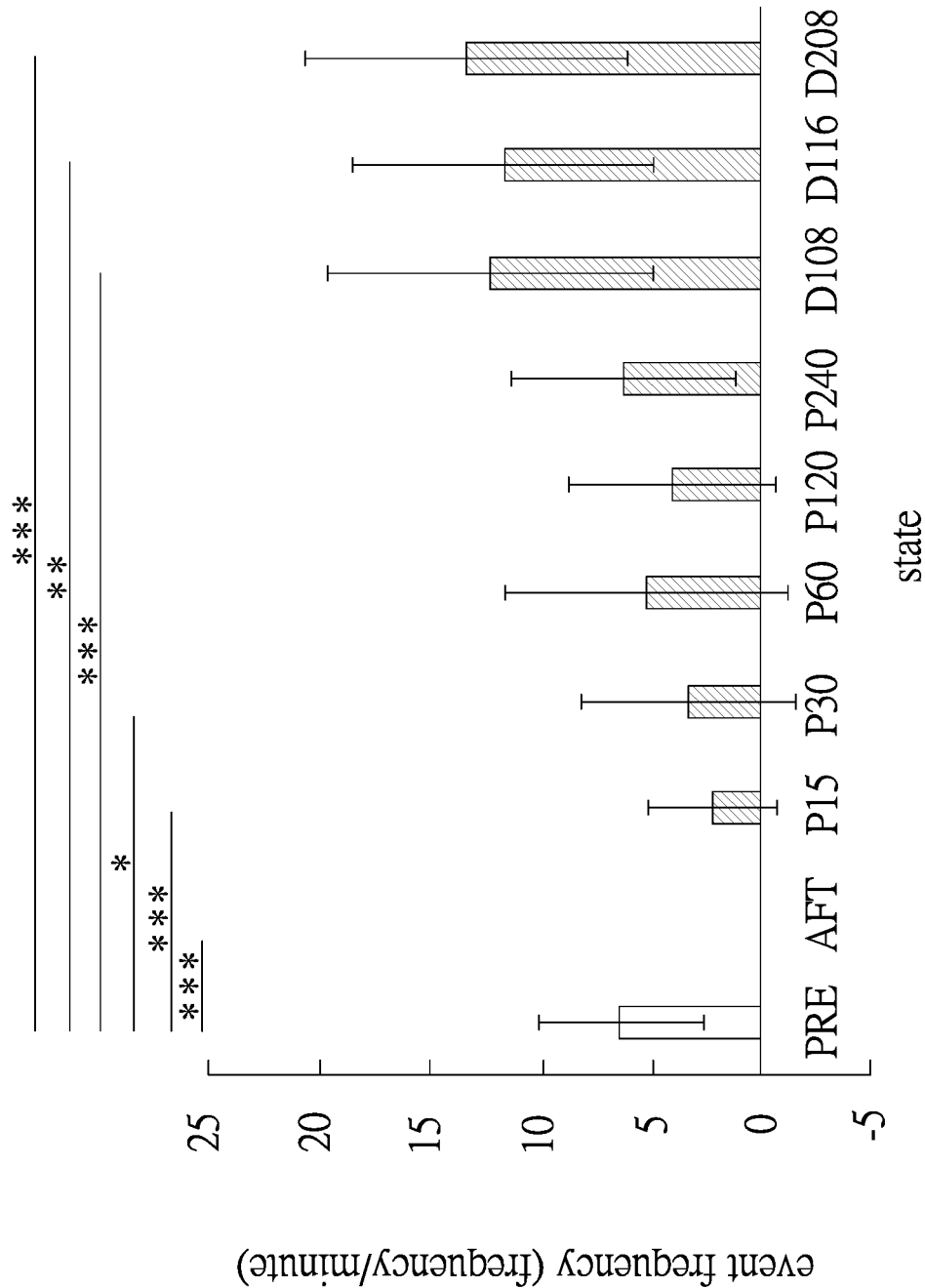
FIG. 5 is a bar graph showing the result of the event frequency corresponding to the bowel recovery at different times after the limb surgery according to an embodiment of the present invention.

Referring to FIG. 1 and FIG. 2, a system in this embodiment includes an audio collection apparatus 1, a signal processing module 2, and a server 3. The audio collection apparatus 1 and the signal processing module 2 are integrated into a portable apparatus.

The audio collection apparatus 1 includes a stethoscope 11, a microphone 12, and an active noise cancellation (ANC) module 13. The signal processing module 2 is connected to the audio collection apparatus 1. The signal processing module 2 includes a preamplification circuit 21, a voltage reference circuit 22, a microprocessor 23, and a first transmission unit 24. The microprocessor 23 has an analog-to-digital converter 231. The server 3 has a processing unit 31 and a second transmission unit 32. The processing unit 31 is in signal communication with the first transmission unit 24 through the second transmission unit 32. In this embodiment, the first transmission unit 24 and the second transmission unit 32 may use any known transmission technology, for example, any one of an infrared transmission module, radio, BLUETOOTH®, ZIGBEE®, 2G, 2.5G, 2.75G, 3G, WI-FI®, and WIMAX®.

Referring to FIG. 1 through FIG. 3, a method in this embodiment is executed by the foregoing system, and includes the following steps:

A. The stethoscope 11 of the audio collection apparatus 1 continuously monitors an abdominal cavity of an examinee within a specific time, and collects a bowel sound signal of an intestinal tract inside the abdominal cavity. The bowel sound signal is converted into an electric signal. In the process, the active noise cancellation module 13 is used to preliminarily filter the noise in the environment. The electric signal is amplified and filtered by the preamplification circuit 21 of the signal processing module 2, and then the electric signal is converted into a digital signal by the analog-to-digital converter 231 of the microprocessor 23. The specific time is set by a doctor or nurse according to different conditions of the examinee. For example, the examinee has received an abdominal surgery, and it usually takes 3 to 5 days for large intestines to restore normal functions after an abdominal surgery; therefore, the specific time may be set to be 3 to 5 days or a longer time. When the audio collection apparatus 1 collects the bowel sound signal, the active noise cancellation module 13 may preliminarily filter environmental noise, and therefore the method may be used in common hospital environments.

B. The first transmission unit 24 of the signal processing module 2 sends out the digital signal, and the processing unit 31 of the server 3 receives the digital signal through the second transmission unit 32. In general, biological signals usually include non-Gaussian biological information and Gaussian noise. A higher-order statistical technology has a characteristic of inhibiting Gaussian noise and keeping non-Gaussian signals; therefore, in the present embodiment, the processing unit 31 removes noise from the digital signal by using higher-order statistics (HOS), and keeps non-Gaussian bowel sound information. The above-mentioned higher-order statistics has been specifically explained in Taiwan Patent No. 1535418 titled "Bowl Sound Analysis Method and System" filed by the inventor and mentioned in the background of the invention, so it won't be described hereinafter.

C. The processing unit 31 captures a high-complexity feature from the digital signal by using a fractal dimension algorithm, and defines the high-complexity feature as an intestinal motility signal. The above-mentioned fractal dimension algorithm has been specifically explained in Taiwan Patent No. 1535418 titled "Bowl Sound Analysis Method and System" filed by the inventor and mentioned in the background of the invention, so it won't be described hereinafter. The difference is that in the embodiment of the present invention, in order to reduce false bowel sound events caused by noise and improve the accuracy of bowel sound detection, the processing unit 31 captures a plurality of local maxima of fractal dimension values, and the sum of the average value and the standard deviation of the local maxima serves as a threshold. When any one of the local maxima of the fractal dimension values exceeds the threshold, it is regarded as a correct intestinal motility signal. In this embodiment, the processing unit 31 captures the local maxima between 40% and 60% of the fractal dimension values for prediction. Experiments have proved that it can cover more than 90% of bowel sound events.

D. In this embodiment, the processing unit 31 captures at least one feature value of the intestinal motility signal and uses artificial intelligence of a linear or non-linear algorithm for training to actively evaluate the intestinal function of the examinee. The feature value may include an event frequency, sound index, ratio of the bowel sounds in clusters, duration, maximum peak value, and center frequency. In this embodiment, the processing unit 31 uses an artificial neural network to evaluate the intestinal function of the examinee. The artificial neural network a three-layer structure containing $N_0$ input neurons, $N_1$ hidden neurons and one output neuron. In terms of evaluating the recovery state of the intestinal function after surgery, in the training phase, the expected outputs of the recovered intestinal function and the unrecovered intestinal function of the artificial neural network are defined as 1 and 0, respectively. According to the clinical experience of medical staff, a judgment threshold between 0 and 1 is given. When the output of the artificial neural network is greater than the judgment threshold, the state of the examinee is determined as a restored state, otherwise, the state of the examinee is determined as an unrecovered state.

Figure 7:
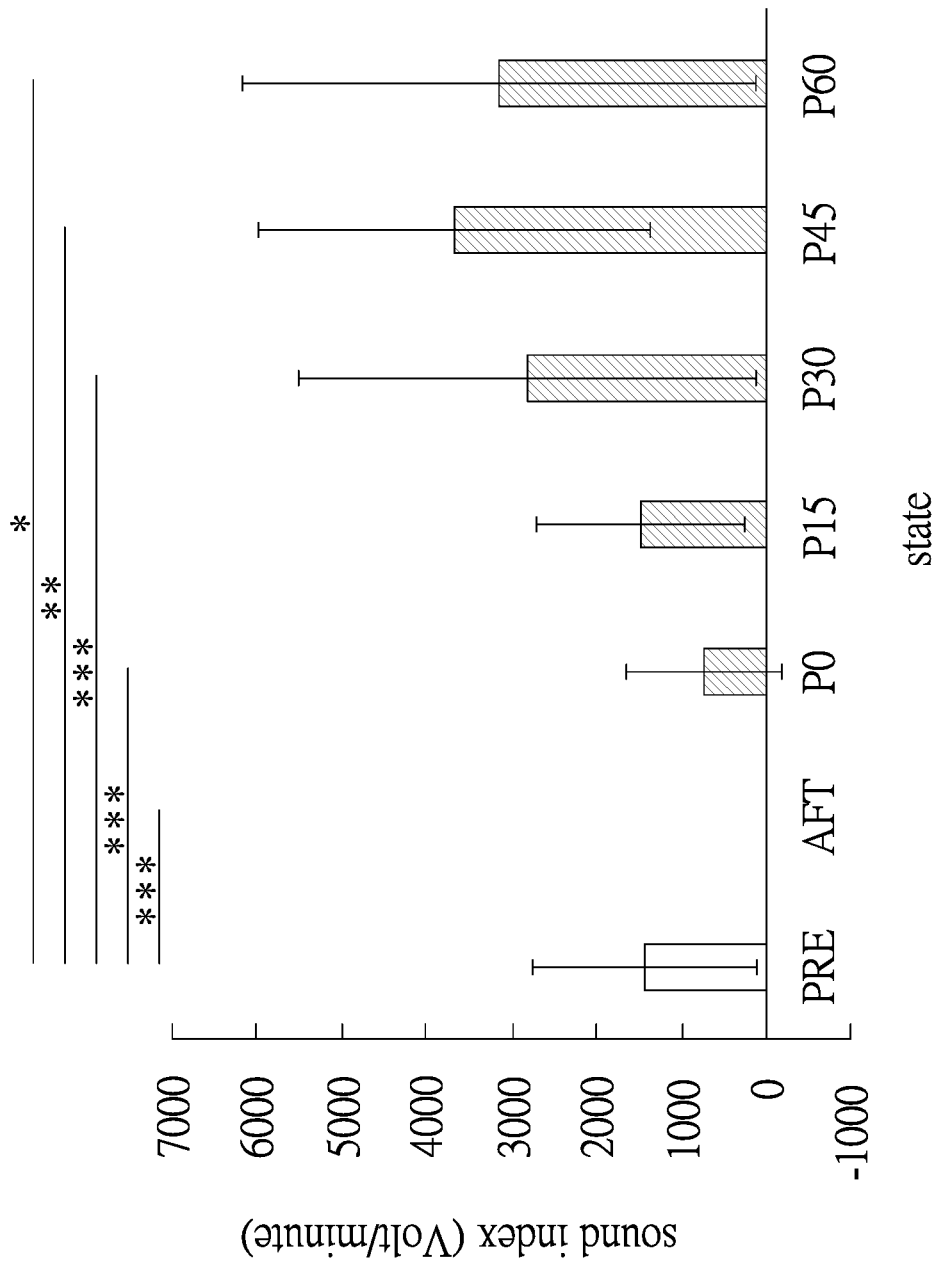
FIG. 7 is a bar graph showing the result of the sound index corresponding to the bowel recovery at different times after the gastrointestinal endoscopic surgery according to an embodiment of the present invention.
Figure 8:
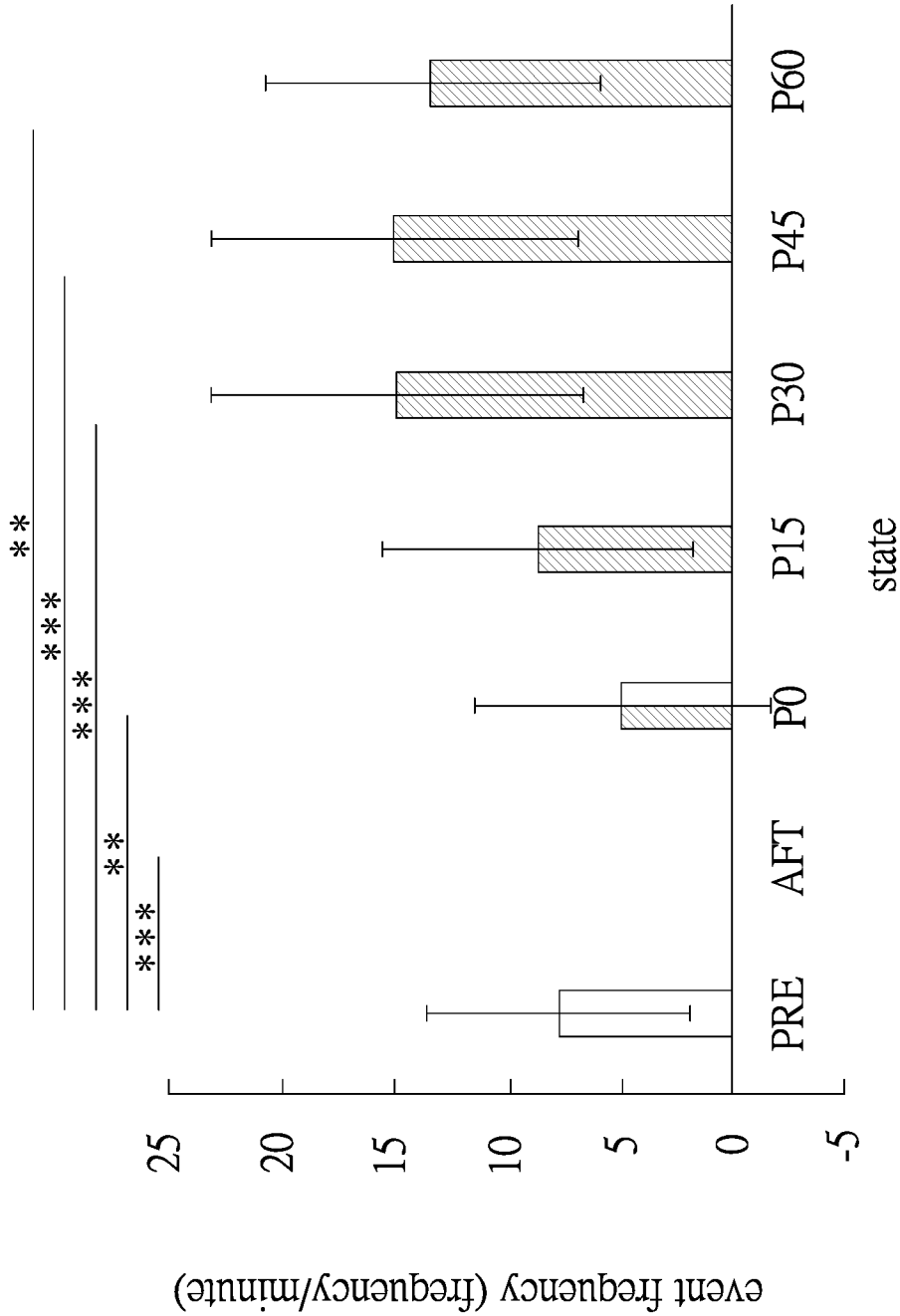
FIG. 8 is a bar graph showing the result of the event frequency corresponding to the bowel recovery at different times after the gastrointestinal endoscopic surgery according to an embodiment of the present invention.
Figure 9:
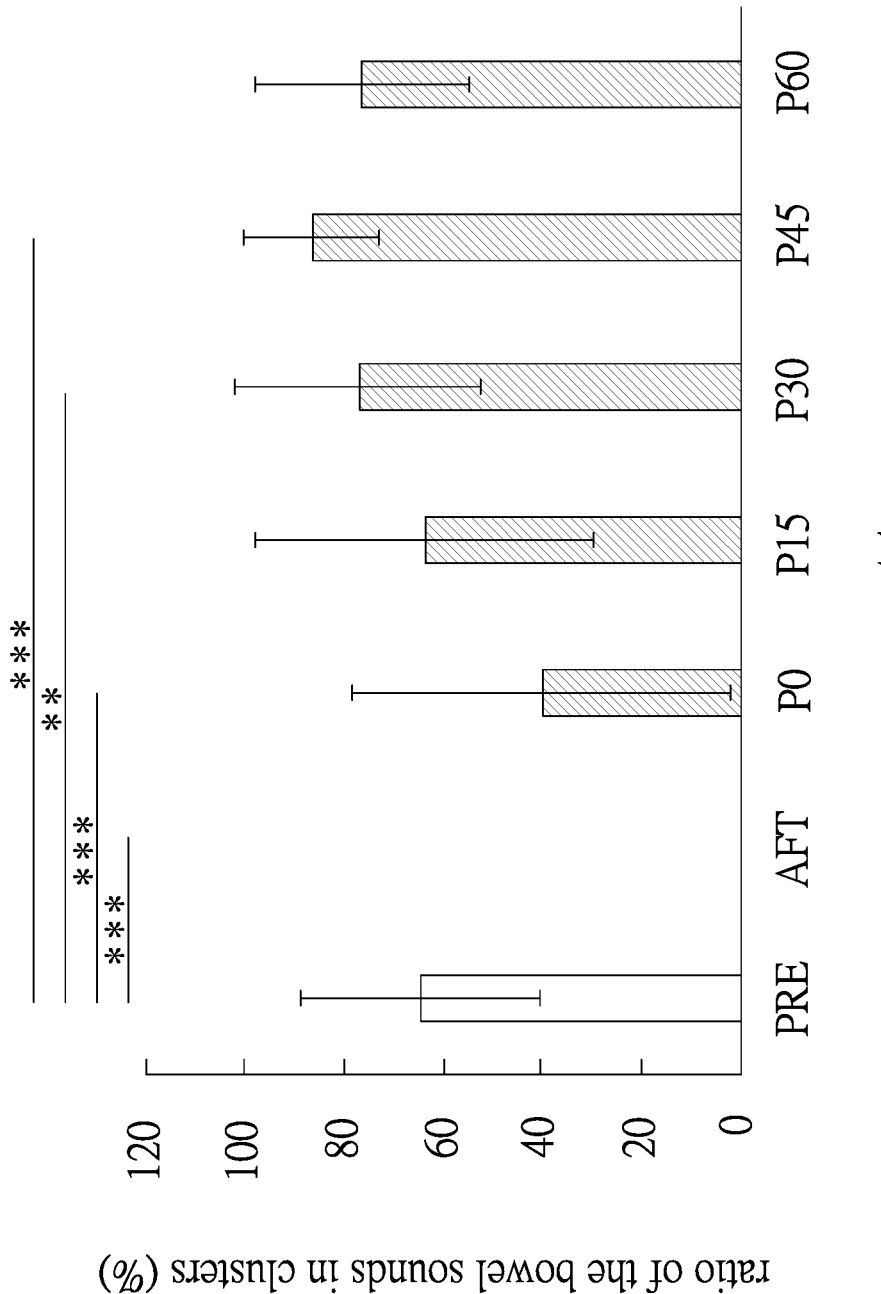
FIG. 9 is a bar graph showing the result of the ratio of the bowel sounds in clusters corresponding to the bowel recovery at different times after the gastrointestinal endoscopic surgery according to an embodiment of the present invention.

In this embodiment, the test was performed on 90 surgical patients at Tainan Chi Mei Medical Center, including 62 patients undergoing gastrointestinal endoscopic surgery (average age 49.00±11.73 years) and 28 patients undergoing limb surgery (average age 60.54±12.98 years). In limb surgery, the bowel sound signals are separately collected for one minute before the operation (PRE), one minute after the induction of general anesthesia (AFT), 15, 30, 60, 120, 240 minutes after entering the recovery room after anesthesia (P0, P15, P30, P45, P60, P120 and P240). The bowel sound signals are collected at 8 a.m. and 4 p.m. (D108 and D116) on the first day after surgery. The bowel sound signals are collected at 8 am (D208) the next day after surgery. As shown FIG. 7 through FIG. 9, in the gastrointestinal endoscopic surgery, the bowel sound signals are collected at PRE, AFT, P0, P15, P30, P45 and P60.

According to experiments, in the feature values captured from the intestinal motility signal, including the event frequency, sound index, ratio of the bowel sounds in clusters, are significantly different between the preoperative state and the postoperative recovery state, and can be used to evaluate the recovery state of the intestinal function after surgery. In the AI determination using an artificial neural network algorithm, the above test cases are classified as true positive (TP, which means that the restored state is correctly classified as the restored state), false positive (FP, which means that the unrecovered state is incorrectly classified as the restored state), true negative (TN, which means that the unrecovered state is correctly classified as the unrecovered state), and false negative (FN, which means that the recovered state is incorrectly classified as the unrecovered state) for testing. Besides, using F measure finds the best judgment threshold, the F measure formula is calculated as:

$$F - \text{measure} = 2 \cdot \frac{\text{recall} \cdot \text{precision}}{\text{recall} + \text{precision}}$$

In the above test result, the artificial neural network is used to predict the feature values, including the event frequency, sound index, ratio of the bowel sounds in clusters in the intestinal motility signal. The number of hidden neurons and the judgment threshold are set to 64 and 0.4 respectively for the best performance. (F measure=83.36%, sensitivity=96.25%, PPV=73.51%, accuracy=79.36%).

The feature values, such as the duration, maximum peak value and center frequency in the intestinal motility signal, can be used to evaluate the symptoms of acute enteritis, intestinal obstruction and irritable bowel syndrome in children according to the test.

The present invention also provides a program product installed to the aforementioned server 3 for executing the aforementioned method of evaluating the intestinal function with bowel sound signals.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A method for evaluating an intestinal function using bowel sounds, comprising the steps of:
   A. continuously monitoring an abdominal cavity of an examinee within a specific time by using an audio collection apparatus, collecting a bowel sound signal of an intestinal tract inside the abdominal cavity, and converting the bowel sound signal into a digital signal;
   B. using higher-order statistics (HOS), by a processing unit, to remove noise from the digital signal;
   C. using a fractal dimension algorithm, by the processing unit, to capture a high-complexity feature from the digital signal within a capturing window, and defining the high-complexity feature as an intestinal motility signal, wherein the processing unit captures a plurality of local maxima of fractal dimension values, a sum of an average value of the local maxima of the fractal dimension values and a standard deviation of the local maxima of the fractal dimension values serves as a threshold, when any one of the local maxima of the fractal dimension values exceeds the threshold, it is regarded as the intestinal motility signal; and
   D. evaluating the intestinal function of the examinee by using an intestinal function algorithm selected from a group consisting of a linear algorithm, a non-linear algorithm and a combination thereof, by the processing unit, according to the intestinal motility signal defined in correspondence to said threshold.

2. The method as claimed in claim 1, wherein in Step C, the processing unit captures the local maxima between 40% and 60% of the fractal dimension values within the capturing window.

3. The method as claimed in claim 1, wherein in Step D, the processing unit captures at least one feature value of the intestinal motility signal for evaluating the intestinal function of the examinee.

4. The method as claimed in claim 3, wherein the processing unit captures an event frequency, a sound index, and a ratio of the bowel sounds in clusters in the feature value to evaluate a postoperative recovery state of the intestinal function.

5. The method as claimed in claim 3, wherein the processing unit captures a duration, a maximum peak value and a center frequency in the feature value to evaluate acute enteritis, intestinal obstruction and irritable bowel syndrome in the examinee, wherein the examinee is a child.

6. The method as claimed in claim 1, wherein the processing unit uses an artificial neural network to evaluate the intestinal function of the examinee, an evaluation value of the artificial neural network is set between 0 and 1, and a number of hidden neurons and a judgment threshold are set to 64 and 0.4, respectively.

7. A system for evaluating an intestinal function using bowel sounds, comprising:
   an audio collection apparatus, including a stethoscope and a microphone, wherein the stethoscope continuously collects a bowel sound signal within a specific time and the microphone converts the bowel sound signal into an electric signal;
   a signal processing module, connected to the audio collection apparatus, the signal processing module including a preamplification circuit, a voltage reference circuit, a microprocessor and a first transmission unit, the microprocessor having an analog-to-digital converter, the preamplification circuit amplifying and filtering the electric signal, the microprocessor converting the electric signal into a digital signal and sending the digital signal through the first transmission unit;
   a server, having a processing unit and a second transmission unit, the processing unit receiving the digital signal from the first transmission unit through the second transmission unit, using higher-order statistics (HOS) to remove noise from the digital signal, using a fractal dimension algorithm to capture a high-complexity feature from the digital signal, and defining the high-complexity feature as an intestinal motility signal; wherein the processing unit captures a plurality of local maxima of fractal dimension values, wherein a sum of an average value and a standard deviation of the local maxima of the fractal dimension values serve as a threshold, and wherein, when any one of the local maxima of the fractal dimension values exceeds the threshold, it is regarded as the intestinal motility signal; the processing unit further evaluating the intestinal function of an examinee according to the intestinal motility signal defined in correspondence to said threshold by using an intestinal function algorithm selected from a group consisting of a linear algorithm, a non-linear algorithm, and a combination thereof.

8. The system as claimed in claim 7, wherein the audio collection apparatus further includes an active noise cancellation module.

9. A program product, installed to a server, for performing a method for evaluating an intestinal function using bowel sounds, comprising:
   A. continuously monitoring an abdominal cavity of an examinee within a specific time by using an audio collection apparatus, collecting a bowel sound signal of an intestinal tract inside the abdominal cavity, and converting the bowel sound signal into a digital signal;
   B. using higher-order statistics (HOS), by a processing unit of the server, to remove noise from the digital signal;
   C. using a fractal dimension algorithm, by the processing unit, to capture a high-complexity feature from the digital signal, and defining the high-complexity feature as an intestinal motility signal, wherein the processing unit captures a plurality of local maxima of fractal dimension values, a sum of an average value of the local maxima of the fractal dimension values and a standard deviation of the local maxima of the fractal dimension values serves as a threshold, when any one of the local maxima of the fractal dimension values exceeds the threshold, it is regarded as the intestinal motility signal; and
   D. evaluating the intestinal function of the examinee by using an intestinal function algorithm selected from a group consisting of a linear algorithm, a non-linear algorithm, and a combination thereof, by the processing unit, according to the intestinal motility signal defined in correspondence to said threshold.

* * * * *